(12) United States Patent
Yu et al.

(10) Patent No.: US 6,294,341 B1
(45) Date of Patent: Sep. 25, 2001

(54) METHOD FOR DETECTING A SUBSTANCE HAVING AN ACTIVITY TO INHIBIT HIV INFECTION USING IMMUNOASSAY AND VARIANT PROTEIN USED FOR SAID METHOD

(75) Inventors: Yeon Gyu Yu, Seoul (KR); Sung-Hou Kim, Berkeley, CA (US); Jae-Ryeon Ryu, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/272,342

(22) Filed: Mar. 19, 1999

(30) Foreign Application Priority Data

Mar. 21, 1998 (KR) .................................... 98-9858

(51) Int. Cl.[7] .................................... G01N 33/53

(52) U.S. Cl. .......................... 435/7.1; 435/7.9; 435/7.92; 435/7.94; 435/974; 436/531; 530/350; 530/826

(58) Field of Search ................................. 435/5, 7.1, 7.9, 435/7.92, 7.94, 974; 436/531; 530/350, 324, 826

(56) References Cited

FOREIGN PATENT DOCUMENTS

92/13955 * 8/1992 (WO).

OTHER PUBLICATIONS

Pharmacia catalog, "Molecular and Cell Biology Catalog 1993".*
David C. Chan, e t al., "Core Structure of gp41 From the HIV Envelope Glycoprotein", Cell, vol. 89, Apr. 18, 1997, pp. 263–273.
C. T. Wild, et al., "Peptides Correspoding to a Predictive –Helical Domain of Human Immunodeficiency Virus Type 1 gp41 Are Potent Inhibitors of Virus Infection", Proc. Natl. Acad. Sci. USA, vol. 91, Oct. 1994, pp. 9770–9974.
W. Weissenhorn, et al., "Atomic Structure of the Ectodomain From HIV–1 gp41", letters to nature, Nature, vol. 387, No. 22, May 1997, pp. 426–430.
D.M. Lambert, et al., "Peptides From Conserved Regions of Paramyxovirus Fusion (F) Proteins Are Potent Inhibitors of Viral Fusion", Proc. Natl. Acad. Sci. USA, vol. 93, Mar. 1996, pp. 2186–2191.
O. Nussbaum, et al., "Fusogenic Mechanisms of Envelope-d–Virus Glycoproteins Analyzed by a Novel Recombinant Vaccinia Virus–Based Assay Quantitating Cell Fusion–Dependent Reporter Gene Activation", Journal of Virology, Sep. 1994, pp. 5411–5422.

* cited by examiner

*Primary Examiner*—Jeffrey Stucker
(74) *Attorney, Agent, or Firm*—Oblon, Spivak, McClelland, Maier & Neustadt, P.C.

(57) ABSTRACT

The present invention relates to a method for detecting a substance having an activity to inhibit HIV infection rapidly, economically and safely. The present invention uses the characteristics that if a function of transmembrane protein gp41 of HIV is inhibited, HIV infection is also inhibited, and therefore the function of gp41 depends on the interaction between two helical structures of gp41. The method of the present invention is to detect a substance to inhibit HIV infection by an immunoassay using the interaction between the variant protein Trx-N, which is prepared by binding the N-terminal helical domain of gp41 to Trx (thioredoxin) and the variant protein GST-C, which is prepared by binding the C-terminal helical domain of gp41 with GST-C (Glutathione S-transferase). This immunoassay can be used for automatic detection of the substance to inhibit the activity of gp41 can be carried out by the method. As a result, it is possible to investigate HIV infection-inhibiting activity of a number of previously known compounds or natural compounds, and it can attribute to the development of therapeutic agent of HIV infection.

2 Claims, 3 Drawing Sheets

METHOD FOR DETECTING A SUBSTANCE HAVING AN ACTIVITY TO INHIBIT HIV INFECTION USING IMMUNOASSAY AND VARIANT PROTEIN USED FOR SAID METHOD

BACKGROUND OF THE INVENTION

1. Field of the Invention

The present invention relates to a method for detecting substances having an activity to inhibit HIV infection. More particularly, the invention relates to an improved method for detecting substances having an activity to inhibit action of gp41, which is responsible for the infection of HIV, in order to develop a therapeutic agent for Acquired Immune Deficiency Syndrome (AIDS). This method is quicker, more economical and safer than the prior art.

2. Description of the Prior Art

HIV Infection is mediated by two types of protein, gp120 and gp41, which present on the envelope membrane of the virus. gp120 recognizes a cell to be infected and induces initial binding to the cell, while gp41 causes the fusion between the envelope membrane of the virus and the cytoplasmic membrane of the cell.

The tertiary structure of these proteins is unknown, but studies of their primary structure revealed that gp41 comprises a fusion peptide (FP) capable of interacting with a target cell membrane, an amino-terminal helical structure (N-αH), carboxy-terminal helical structure (C-αH), a transmembrane segment (TM) and a cytoplasmic domain as shown in FIG. 1. In FIG. 1, the fusion peptide (FP) is represented by a black square, both helical structure N-αH and C-αH are represented by gray squares, and transmembrane segment (TM) is represented by a black square.

The peptides derived from two helical region of the ectodomain of gp41 outside the cell strongly bind to each other to form a stable six-helical bundle complex composed of a trimer of two interacting peptides (See, Chan et al., Cell 89, 263–273, 1997). It is presumed that the interaction of two helical domains plays a key role in the structural stability or function of the gp41 protein. Therefore, a substance that can inhibit the interaction between two helical structures of the gp41 proteins may inhibit HIV infection by inhibiting the action of gp41. Thus, the substance can be utilized as a therapeutic agent for AIDS.

The substances having such inhibitory activity include, for example, peptides derived from two helical domains of gp41 (See, Wild et al., Pro. Natl. Acad. Sci. USA 91, 9770–9774, 1994). These peptides bind to one of the two helical domains to inhibit binding or interaction between the two helical structures of gp41. Consequently, they inhibit the function of gp41 and, as a result, inhibit HIV infection. Therefore, if a method that easily detects the interaction between two helical domains of gp41 is developed, such method will be able to be used to detect substances that inhibit the function of gp41 or HIV infection.

Currently used methods for detecting substances to inhibit the function of gp41 use a system comprising culturing an animal cell in which receptors of gp120 are expressed, infecting the cell with HIV or vaccinia virus harboring env gene encoding gp 120 and gp41, and inducing cell fusion between the infected cells (See, Nussbaum et al., J. Virol. 68, 5411–5422, 1994). Anti-HIV activity of a substance is measured by investigating the inhibitory effect on the fusion between cells infected with HIV or a vaccinia virus. However, this method has the following problems: First, it is complex, difficult to carry out and requires the animal cell culture, which is expensive. Second, since it uses a living HIV or vaccinia virus, there is a possibility that an experimenter could be exposed to or infected with the harmful virus. Moreover, special expensive equipment is required for preventing such infection. Third, in addition to the considerable amount of time that is required to culture the cell, since numerous processing steps are required as well, it is difficult to screen a number of compounds that can inhibit gp41. That is, the known method for detecting a substance to inhibit the activity of gp41 is expensive, time consuming and requires special equipment. Therefore, there exists the need for a safe, inexpensive, easily manageable and time efficient method for detecting an inhibitor of gp41 activity from the known compounds.

Considering the problems associated with conventional methods, the present inventors investigated a method for rapidly, economically and safely detecting a substance having an inhibitory activity of HIV infection. As the result, the present inventors found that a substance capable of inhibiting gp41 activity can be detected by using the interaction between one variant protein, Trx-N, and another variant protein, GST-C, wherein Trx-N is prepared by connecting the N-terminal helical domain of gp41 to Trx (thioredoxin), and GST-C is prepared by connecting the C-terminal helical domain of gp41 to GST (Glutathione S-transferase).

Therefore, the method of the invention comprises preparing the variant proteins, identifying the presence of interaction between the two helical domains of gp41 by determining the interaction between two variant proteins, developing immunoassay using two variant proteins having such interaction and detecting a substance having an inhibitory activity of HIV infection by the immunoassay.

SUMMARY OF THE INVENTION

It is an object of the invention to provide variant protein Trx-N (SEQ ID NO:6) which is prepared by connecting the N-terminal helical domain of gp41 (amino acids of SEQ ID NO:7) to Trx ( SEQ ID NO:5) (thioredoxin).

It is a further object of the invention to provide variant protein GST-C, which is prepared by connecting the C-terminal helical domain of gp41 (amino acids 89–157 of SEQ ID NO:7) to GST (SEQ ID NO:7) to GST (SEQ ID NO:3) (Glutathione S-transferase).

It is a further object of the invention to provide a method for detecting a substance having an activity to rapidly inhibit action of gp41, which is responsible for the infection of HIV, in order to rapidly develop a therapeutic agent for AIDS.

According to the method of the present invention, it is possible to rapidly, economically and safely detect a substance capable of inhibiting HIV infection.

DETAILED DESCRIPTION OF THE INVENTION

The present invention provides the variant protein Trx-N (SEQ ID NO:6), which is prepared by connecting the N-terminal helical domain of gp41 (amino acids 34–84 of SEQ ID NO:7) to Trx (SEQ ID NO:5) (thioredoxin), and variant protein GST-C, which is prepared by connecting the C-terminal helical domain of gp41 (amino acids 89–157 of SEQ ID NO:7) to GST (SEQ ID NO:8) (Glutathione S-transferase). Furthermore, the present invention relates to a method for detecting a substance having an inhibitory activity against HIV infection.

The present invention is described in detail below.

(1) Preparation of the Variant Proteins

Figure 1:
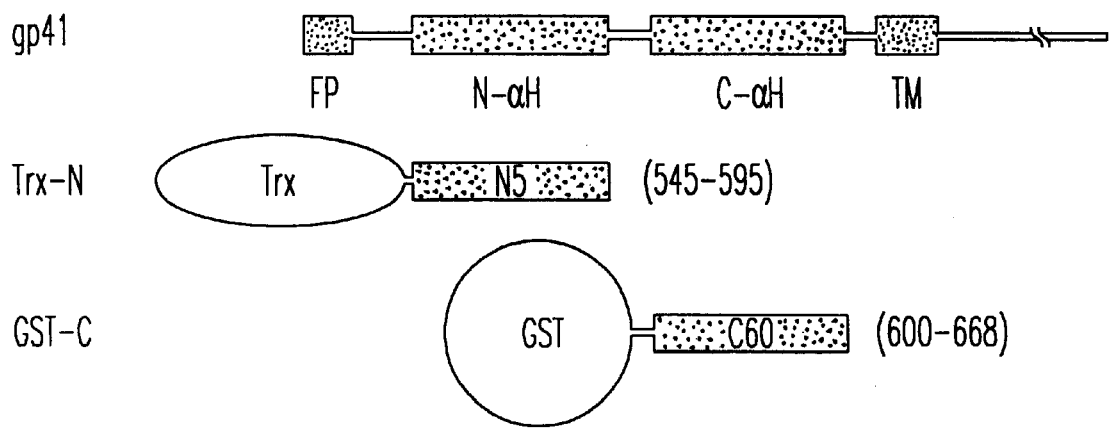
FIG. 1 shows structures of gp41 and two variant proteins (Trx-N and GST-C).

To imitate the interaction between two helical domains of gp41, the variant proteins, in which each of two helical domains of gp41 is attached to a different protein, are prepared as follows:

A DNA fragment corresponding to an amino terminal helical domain (amino acid 34–84 of SEQ ID NO:7) of gp41 is amplified by a polymerase chain reaction (PCR) from a plasmid having an env gene of HIV. The amplified DNA is ligated to the carboxy terminus of thioredoxin (Trx) (SEQ ID NO:5) of pTrxFus (Invirogen, U.S.A.) plasmid DNA from which the thioredoxin variant protein (SEQ ID NO:6) (hereinafter, "Trx-N") as shown in FIG. 1 is expressed. In the same manner, a DNA fragment corresponding to the carboxy terminal helical domain (amino acid 89–157 of SEQ ID NO:7) of gp41 is amplified by PCR and then is ligated to the carboxy terminus of glutathione S-transferase (SEQ ID NO:8) (GST; Pharmacia) of pGEX-2T plasmid, which expresses the glutathione transferase variant protein (hereinafter, "GST-C" (SEQ ID NO:9)). The relationship between each domain of gp41 and the prepared variant proteins is shown in FIG. 1. The two variant proteins are expressed in *E. coli* and then isolated and purified by ion exchange chromatography or affinity chromatography using a glutathione-resin. The isolated proteins are identified as being at least 95% pure.

(2) Determination of the Interaction Between the Variant Proteins

The interaction of the two variant proteins as prepared above is identified by the chromatography method. Unmodified Trx does not interact with unmodified GST. Thus, two independent peaks are detected when a mixture of them is analyzed by gel permeation chromatography. When GST-C and Trx-N variant proteins, in which two helical regions of gp41 are incorporated, are mixed, a new peak having increased size by the interaction between two variant proteins is detected by the gel permeation chromatography (See, FIG. 2). Thus, this result shows that the interaction between two helical domains of gp41 is also present in the variant proteins.

(3) Development of Immunoassay Using the Variant Proteins

The immunoassay is carried out by using the interaction of two variant proteins as prepared above. This immunoassay comprises the step of adsorbing a Trx-N variant protein on the surface of a plastic cell culture vessel and then adding GST-C; the step of removing GST-C, which is not bound to Trx-N, and then adding a primary antibody (anti-GST Ab) having a selectivity on GST; the step of removing the primary antibody which is not bound to GST-C and then adding a secondary antibody (anti-Goat Ab) which recognizes the primary antibody; the step of removing the secondary antibody which is not bound to the primary antibody and then adding peroxide ($H_2O_2$) and OPD (o-phenylenediamine), which are the substrates of peroxidase; and the step of determining the color development of OPD oxidized by peroxidase, which is chemically bound to the secondary antibody.

Figure 3:
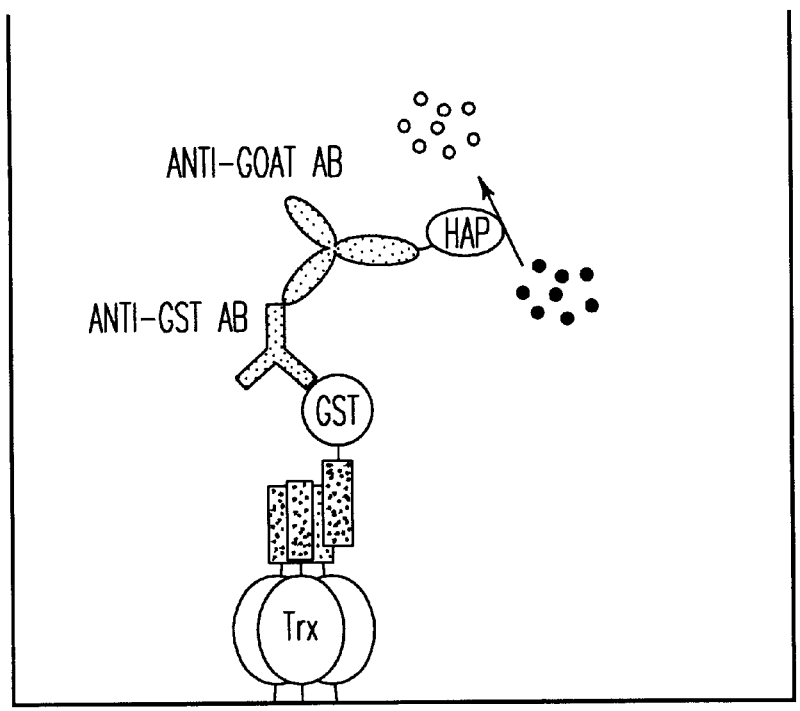
FIG. 3 is a schematic diagram showing a method for determining the binding between Trx-N and GST-C by a immunoassay.

As shown in FIG. 3, a Trx-N variant protein is adsorbed on the surface of a plastic cell culture vessel and then aqueous GST-C solution is added. At this time, a GST-C variant protein is bound to Trx-N protein adsorbed on the surface of the vessel. The GST-C that is not bound to Trx-N is removed and a primary antibody (anti-GST Ab) which has specificity for GST is added so that the antibody can recognize the GST-C protein that is bound to the Trx-N protein. The primary antibody which is not bound to GST-C is removed and then a secondary antibody (anti-Goat Ab), which recognizes the primary antibody, is added in order to bind to the primary antibody, which is bound to GST-C. The secondary antibody, which is not bound to the primary antibody, is removed and then peroxide ($H_2O_2$) and OPD (o-phenylenediamine), which are the substrates of peroxidase, are added. Thereafter, the binding of two variant proteins is identified by determining the color development of OPD oxidized by the peroxidase that is chemically bound to the secondary antibody.

(4) Detection of a Substance Having an Activity to Inhibit HIV Infection by the Immunoassay It is investigated he possibility that the immunoassay of the present invention can be used for detecting a substance which can inhibit the function of gp41 and thus inhibit the infection of HIV.

The Detection of a substance having an activity to inhibit HIV infection comprises the step of adsorbing a Trx-N variant protein on the surface of a plastic cell culture vessel and then adding GST-C and a substance to be detected; the step of removing GST-C which is not bound to Trx-N and then adding a primary antibody (anti-GST Ab) having a selectivity on GST; the step of removing the primary antibody which is not bound to GST-C and then adding a secondary antibody (anti-Goat Ab), which recognizes the primary antibody; the step of removing the secondary antibody which is not bound to the primary antibody and then adding peroxide ($H_2O_2$) and OPD (o-phenylenediamine), which are the substrates of peroxidase; the step of determining the color development of OPD oxidized by peroxidase which is chemically bound to the secondary antibody; and the step of comparing the color development value of OPD as determined with that of OPD when determined without adding the substance to be detected.

Peptides having amino acid sequences of the carboxy terminal helical domain of gp41 are known to have a very effective activity to inhibit HIV infection. There, peptides inhibit HIV infection at concentrations of 1 nM to 1 $\mu$M. It is presumed that their activities to inhibit HIV infection is attributed to the function of peptides, which bar the interaction between two helical structures of gp41 to decrease the stability of gp41 or inhibit the structural change of gp41 that is required for cell membrane fusion (See, Weissenhorn et al., Nature 387, 426–430, 1997). Peptides derived from the helical domain of gp41 will inhibit the interaction between GST-C and Trx-N, and their inhibitory activities can be easily detected by the immunoassay described above.

The advantages of the present invention's method for detection as compared to currently known methods are as follows: First, it can be performed easily at low cost. Second, since it uses proteins, unlike prior art methods that use a living HIV or vaccinia virus, there is no danger of the experimenter becoming infected with the virus, and therefore the activity of substance to inhibit HIV infection can be detected with safety. Third, gp41-inhibiting activities of a number of compounds can be simultaneously detected. In summary, the method of the present invention can detect a number of compounds in a shorter time, at lower expense and more safely than other known methods.

In addition, the detecting method of the present invention is also applicable with viral diseases other than HIV. Viruses that induce pneumonia or measles have proteins involved in cell membrane fusion, such as gp41 in HIV, which are presumed to have a structure and mechanism similar to gp41 (See, Lambert et al., Proc. Natl. Acad. Sci, USA 93, 2186–2191, 1996). More specifically, a peptide having a helical structure immediately adjacent to the transmembrane domain that is outside the cell membrane has properties that inhibit the infection of viruses. Therefore, by using the principle of the method described in the specification of the application, a method for detecting a substance to inhibit the infection of specific viruses can be developed.

Furthermore, by using the immunoassay of the present invention, an automatic method for detecting a substance to inhibit HIV infection can be developed. Any one of Trx-N and GST-C proteins having N- and C-terminal helical domains of gp41, respectively, is bound to a substance which emits an excited electron when a certain wavelength of light is radiated thereon (for example, Eu-trisbipyridine cryptate which receives a 337 nm wavelength of light and emits an excited electron), and the other variant protein is bound to a substance that absorbs emitted electron and produces certain wavelengths of fluorescence (for example, allophycocyanin KL-665, which roduces fluorescence with a wavelength of 665 nm).

In order for the excited electron to stimulate the fluorescent substance that produces fluorescence, two proteins must be present within close proximity of each other. That is, a secondary fluorescence can be produced only when two proteins form a complex. Therefore, if the substance emitting the excited electron and the substance absorbing the emitted electron and producing the fluorescence are chemically bound to Trx-N and GST-C, respectively, and these compounds are mixed, the Trx-N protein binds to the GST-C protein and the electron-emitting substance and the fluorescence-producing substance can be thought to be in close proximity of each other. If a light is radiated to the complex at a wavelength to excite the electron, fluorescence is obtained.

The addition of a substance that inhibits the formation of a complex between two variant proteins will also inhibit the production of the fluorescence. By comparing a fluorescence value that is determined by adding a substance to be detected with that which is determined without adding a substance to be detected, the substances that inhibit the binding between two variant proteins can be detected in the aqueous phase. Because the multi-step washing process is not required with this method and the binding reaction between two variant proteins and the detection of the fluorescence can be accomplished within several seconds, an activity to inhibit HIV infection could be detected automatically. Therefore, the activity to inhibit HIV infection of a number of compounds can be determined in a simple and easy manner.

DESCRIPTION OF THE PREFERRED EMBODIMENTS

The present invention will be illustrated in greater detail in the following examples. The examples are presented only for illustrative purposes and should not be construed as limiting the invention.

EXAMPLE 1

Preparation of Gene Encoding Trx-N

A DNA fragment encoding amino terminal helical domain (amino acid 545–595) of gp41 was amplified by repeating a polymerase chain reaction (PCR) 25 times (at 95° C. for 1 min; at 55° C. for 1 min; 72° C. for 1 min/cycle) from pENV plasmid containing env gene of HIV. The primers that were used in PCR have the following nucleic acid sequences:

5' primer: 5'-CCGGCCTCTAGAATTGTCTGGTAT AGTGCAGCAG-3' (SEQ ID NO:1)
3' primer: 5'-CGGGCCCTGCAGTCAAATCCC TAGGAGGAGCTGTTGAT-3' (SEQ ID NO:3)

The amplified DNA was digested with restriction enzymes XbaI and PstI and then ligated to plasmid pTrxFus, which was digested by the same restriction enzymes, using T4 DNA ligase, to prepare an expression vector pTrxN, which produces Trx-N variant protein. The base sequence of the synthesized DNA and confirmation of whether the synthesized DNA was ligated properly to the plasmid pTrx-Fus were identified by determining the base sequence of the plasmid pTrxN.

EXAMPLE 2

Expression, Isolation and Purification of Trx-N Variant Protein

*E. coli* GI724 was transformed with pTrxN, which is the expression vector of Trx-N variant protein, and cultured with shaking in an expression medium ($Na_2HPO_4$ 6 g, $KH_2PO_4$ 3 g, NaCl 0.5 g, $NH_4Cl$ 1 g, casamino acid 2 g, $MgCl_2$ 0.095 g, dextrose 5 g) under 37° C. When $OD_{600nm}$ of the culture medium reached 0.6, tryptophan was added so as to be 0.5 mM of the final concentration, inducing expression of the Trx-N protein. Thereafter, *E. coli* GI724 was further cultured for 5 hours and then collected by centrifugation. *E. coli* GI724 was suspended in a Tris-HCl buffer solution (50 mM Tris-HCl, 50 mM NaCl, pH 8.0) and then passed through a French Press (SML Instrument Inc, U.S.A.) under 12,000 psi so as to destroy the cell wall of the microorganism. The expressed Trx-N was precipitated with 20% ammonium sulfate. Q-sepharose anion exchange resin was used to isolate and purify the expressed Trx-N protein from the precipitate. The purity of the protein prepared by this procedure is approximately 95%.

EXAMPLE 3

Preparation of Gene Encoding GST-C

A DNA encoding carboxy terminal helical domain (amino acid 600–668) of gp41 was amplified by repeating a polymerase chain reaction (PCR) 25 times (at 95° C. for 1 min; at 55° C. for 1 min; 72° C. for 1 min/cycle) from pENV plasmid that contains env gene of HIV. The primers that were used in PCR have the following nucleic acid sequences:

5' primer: 5 '-CAAGGAATTCAAGGATCCATGGGA AAACTCATTTGCACCACTGCT-3' (SEQ ID NO:3)
3' primer: 5'-CTTAGAATTCCGAGTTAACTTGCC CATTTATCTAATTCC-3' (SEQ ID NO:4)

The amplified DNA was digested with restriction enzymes BamHI and EcoRI and then ligated to plasmid pGEX-2T which was digested by the same restriction enzymes using T4 DNA ligase to prepare an expression vector pGSTC which produces GST-C variant protein. The base sequence of the synthesized DNA and confirmation of whether the synthesized DNA was ligated properly to plasmid pGEX-2T were identified by determining base sequence of plasmid pGSTC.

EXAMPLE 4
Expression, Isolation and Purification of GST-C Variant Protein

E. coli DH5α was transformed with pGSTC, which is the expression vector of a GST-C variant protein, and cultured with shaking in LB medium containing 100 μg/ml of ampicillin at 37° C. When $OD_{600nm}$ of the culture medium reached 0.6, IPTG(isopropyl-b-thiogalactoside) was added so as to be 0.5 mM of the final concentration, inducing expression of the GST-C variant protein. Thereafter, E. coli DH5α was further cultured for 3 hours and then collected by centrifugation. E. coli DH5α was suspended in a Tris-HCl buffer solution (50 mM Tris-HCl, 50 mM NaCl, pH 8.0) and then passed through a French Press under 12,000 psi so as to destroy the cell wall of the microorganism. The inclusion body of the expressed GST-C was collected by centrifugation. The inclusion body was solubilized with 8M aqueous solution of urea and an excessive amount of urea was removed by dialysis. Thereafter, the GST-C protein was purified by using a glutathione affinity resin. The purity of the prepared protein was at least 95%.

EXAMPLE 5
Determination of Binding Between Two Variant Proteins by Gel Permeation Chromatography Trx, GST, Trx-N and GST-C were each prepared in a concentration of 1 mg/ml and the proteins were agitated in equal molar ratio. The mixed solution of the proteins were analyzed by HPLC using gel permeation chromatography column (QHP, Shimatzu, Japan). The proteins were detected by determining an optical density at 280 nm.

Figure 2:
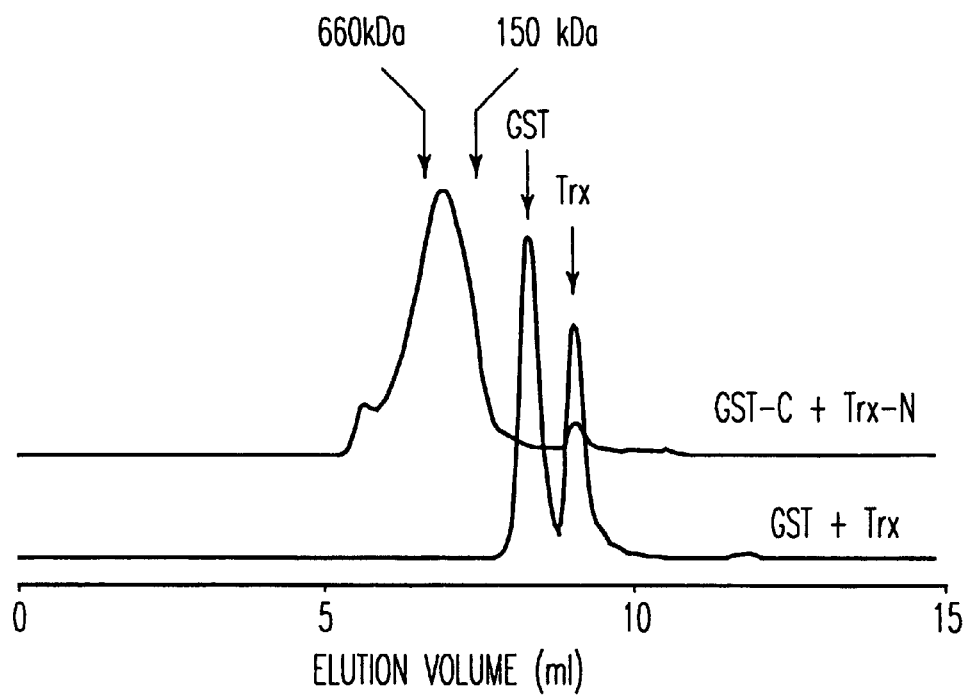
FIG. 2 is a graph showing the result of determining the binding between Trx-N and GST-C by gel chromatography.

As shown in FIG. 2, since unmodified Trx does not interact with unmodified GST, two independent peaks corresponding to Trx and GST were detected. GST-C variant protein having the C-terminal helical domain of gp41 interacts with Trx-N variant protein having N-terminal helical domain of gp41 so that a peak of the complex with increased size was detected. These results show that the interaction between two helical domains of gp41 was also present in the variant proteins.

EXAMPLE 6
Determination of the Interaction Between the Trx-N and GST-C Variant Proteins by the Immunoassay 0.1 ml of a Trx-N protein (2 μg/ml) in 10 mM Tris-HCl (pH 8.0) was introduced into a 96-well cell culture vessel and then was kept at room temperature for 4 hours or at 4° C. for 12 hours so as to adsorb the protein on the surface of the vessel.

The aqueous solution of the protein was removed from the vessel and the vessel was treated with a 5% aqueous solution of skim milk powder at room temperature for 1 hour. After the vessel was washed with an aqueous solution of PBST (100 mM $NaPO_4$, 150 mM NaCl, pH7.0, 0.5% Tween 20) 6 times, 0.1 ml of GST-C protein (3 μg/ml) was added and was subject to reaction with the protein in the vessel at room temperature for 1 hour.

The aqueous solution of the protein was removed and washed with washing solution 6 times, and then 0.1 ml of a primary antibody (anti-GST antibody) against GST-C protein (1/2,000 dilution) was added and was subject to reaction with the substances in the vessel at room temperature for 1 hour.

The aqueous solution of the antibody was removed and washed with the washing solution 6 times, and then 0.1 ml of a secondary antibody (anti-Goat antibody to which peroxidase is bound) against the primary antibody (1/2,000 dilution) was added and was subject to reaction with the substances in the vessel at room temperature for 1 hour.

After removing the aqueous solution of the antibody and washing the vessel with the washing solution 6 times, 0.1 ml of aqueous solution of peroxidase substrate containing 1 mg/ml of OPD (Pierce, U.S.A.) was added and was subject to reaction with the substances in the vessel for 5 to 10 minutes. 0.1 ml of 2.5 M sulfuric acid was added so as to stop the reaction in the vessel, and an optical density of the solution at 496 nm was determined.

Figure 4:
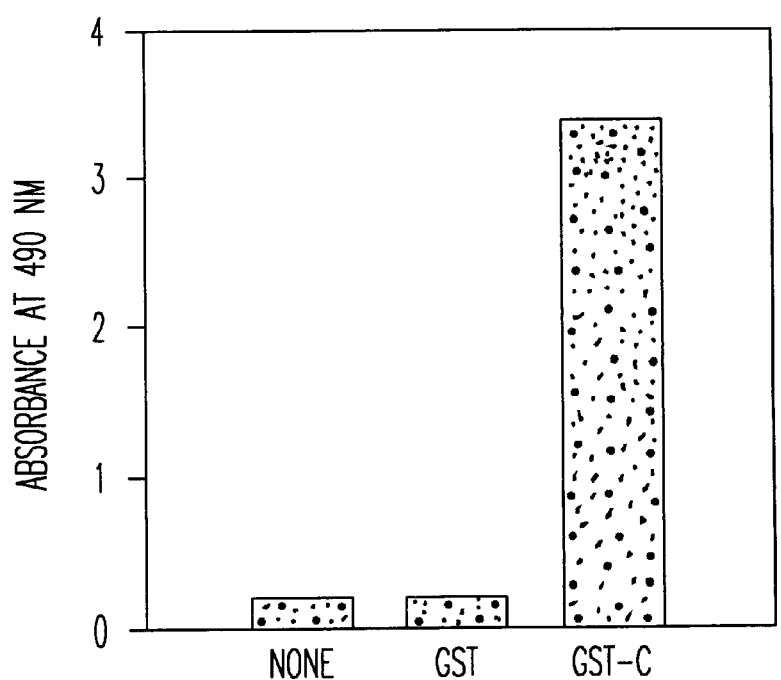
FIG. 4 is a graph showing a specificity of the immunoassay of the present invention.

In order to identify whether this immunoassay can determine selectively the binding between two helical domains of gp41, a presence of the color development reaction by the primary antibody and the secondary antibody to which peroxidase was bound was investigated in cases where the adsorbed Trx-N protein was treated with no protein, treated with GST protein and treated with the GST-C protein. As shown in FIG. 4, only when the Trx-N protein was treated with the GST-C protein (GST-C), did the color development reaction increase. When it was treated with GST (GST), the reaction did not increase like the case of adding no protein (None). These results show that the color development in the immunoassay results from an interaction between two helical domains of gp41 which are present in the variant proteins.

EXAMPLE 7
Preparation of C51 Peptide

A DNA encoding extracellular domain of gp41 was amplified from plasmid pLTRENV containing a gp41 gene of HIV by PCR and inserted into pET21a (Novagen Inc., U.S.A.), which is an expression vector that functions in E. coli.

The prepared expression vector was used to transform E. coli BL21(DE3) and to express the desired protein. After the protein was collected in the form of an insoluble precipitate, the precipitate was liquidized with 8M aqueous solution of urea, and an excessive amount of urea was removed by dialysis. Thereafter, an anion exchange resin was used to prepare the protein (gp41 -ex) with at least 95% of purity.

After the purified protein was treated with trypsin, which is a protein-degrading enzyme, a C51 peptide corresponding to carboxy terminal amino acid 618–660 of gp41 among the resultant peptide was purified by PHLC using C18 column.

EXAMPLE 8
Determination of Inhibitory Activity of C51 Peptide

C51, which represents the carboxy terminal helical region of gp41 as prepared in Example 7, was used to investigate a degree of color development depending on concentration change of C51. In the above immunoassay, GST-C and C51 were added simultaneously to a vessel to the surface of which Trx-N was adsorbed. An activity of C51 to inhibit the binding between Trx-N and GST-C was then determined by comparing the color development of OPD both prior to and after the addition of C51.

Figure 5:
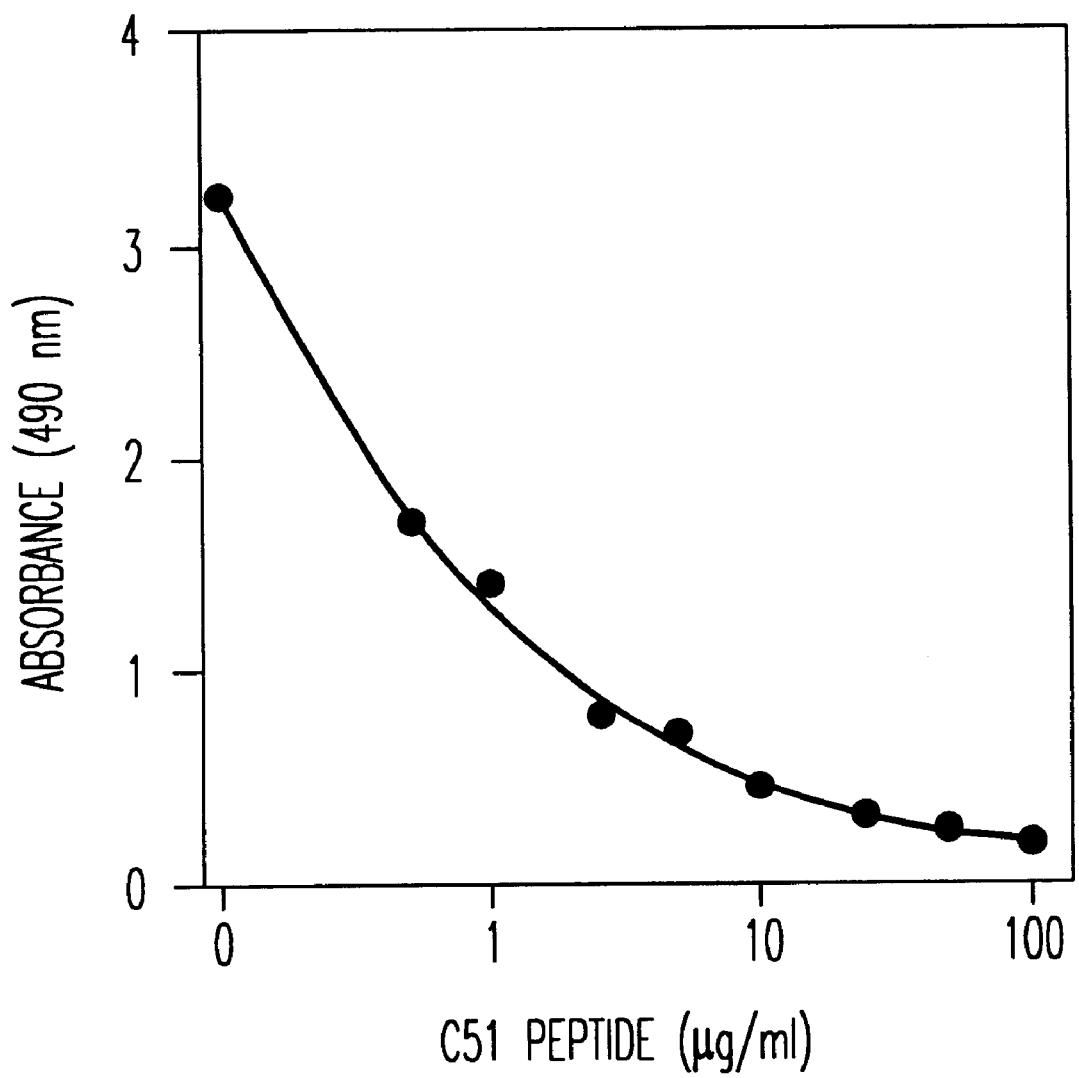
FIG. 5 is a graph showing an activity of an HIV infection-inhibiting peptide determined by the immunoassay of the present invention.

As shown in FIG. 5, the C51 peptide was shown to inhibit binding between GST-C and Trx-N adsorbed on the surface of the vessel in proportion to its concentration. Especially, the C51 peptide showed 50% of the inhibitory percentage in a concentration of 1 μg/ml, from which it can be known that the peptide is a substance to effectively inhibit the binding between GST-C and Trx-N. Further, the peptide showed the activity to inhibit 90% of the cell fusion mediated by the surface protein of HIV in a concentration of 1 μg/ml. Therefore, the immunoassay of the present invention is available for detecting a substance to inhibit HIV infection by inhibiting the function of gp41 to mediate HIV infection.

As discussed the above, according to the method of the present invention for detecting substances that will inhibit HIV activity, it is possible to detect a substance capable of inhibiting HIV infection more rapidly, economically and safely than the methods of the prior art.

What is claimed is:

1. An immunoassay for detecting the presence of GST-C bound to Trx-N comprising:

adsorbing Trx-N variant protein (SEQ ID NO:6) on a surface of a cell culture vessel;

adding GST-C (SEQ ID NO:9);

removing GST-C which is not bound to Trx-N;

adding a primary antibody which binds to GST;

removing the primary antibody which is not bound to GST-C;

adding a secondary antibody which binds to the primary antibody;

removing the secondary antibody which is not bound to the primary antibody;

adding peroxide and o-phenylenediamine; and detecting the color development of o-phenylenediamine oxidized by peroxidase which is chemically bound to the secondary antibody.

2. A method for detecting a substance which inhibits an activity of gp41 comprising:

adsorbing Trx-N variant protein (SEQ ID NO:6) on a surface of a cell culture vessel;

adding GST-C (SEQ ID NO:9) and the substance to be detected;

removing GST-C which is not bound to Trx-N;

adding a primary antibody which binds to GST;

removing the primary antibody which is not bound to GST-C;

adding a secondary antibody which binds to the primary antibody;

removing the secondary antibody which is not bound to the primary antibody;

adding peroxide and o-phenylenediamine;

detecting the color development of o-phenylenediamine oxidized by peroxidase which is chemically bound to the secondary antibody; and comparing the color development value with the color obtained in the absence of the substance to be detected.

* * * * *

SEQUENCE LISTING

```
<160> NUMBER OF SEQ ID NOS: 9

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
ccggcctcta gaattgtctg gtatagtgca gcag                                   34

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
cgggccctgc agtcaaatcc ctaggagctg ttgat                                  35

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
caaggaattc aaggatccat gggaaaactc atttgcacca ctgct                       45

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
cttagaattc cgagttaact tgcccattta tctaattcc                              39

<210> SEQ ID NO 5
<211> LENGTH: 134
<212> TYPE: PRT
<213> ORGANISM: Homo sapiens

<400> SEQUENCE: 5

Met Ser Asp Lys Ile Ile His Leu Thr Asp Asp Ser Phe Asp Thr Asp
  1               5                  10                  15

Val Leu Lys Ala Asp Gly Ala Ile Leu Val Asp Phe Trp Ala Glu Trp
                 20                  25                  30

Cys Gly Pro Cys Lys Met Ile Ala Pro Ile Leu Asp Glu Ile Ala Asp
             35                  40                  45
```

```
Glu Tyr Gln Gly Lys Leu Thr Val Ala Lys Leu Asn Ile Asp Gln Asp
        50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
                100                 105                 110

Ser Gly Asp Asp Asp Lys Val Pro Gly Asp Pro Leu Glu Ser Thr
            115                 120                 125

Cys Ser Asn Arg Thr Gly
        130

<210> SEQ ID NO 6
<211> LENGTH: 177
<212> TYPE: PRT
<213> ORGANISM: homo sapiens and HIV hybrid

<400> SEQUENCE: 6

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
                 20                  25                  30

Cys Gly Pro Cys Lys Met Ile Ala Pro Ile Leu Asp Glu Ile Ala Asp
                 35                  40                  45

Glu Tyr Gln Gly Lys Leu Thr Val Ala Lys Leu Asn Ile Asp Gln Asp
        50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
                100                 105                 110

Ser Gly Asp Asp Asp Lys Val Pro Gly Asp Pro Leu Glu Leu Ser
            115                 120                 125

Gly Ile Val Gln Gln Gln Asn Asn Leu Leu Arg Ala Ile Glu Ala Gln
        130                 135                 140

Gln His Leu Leu Gln Leu Thr Val Trp Gly Ile Lys Gln Leu Gln Ala
145                 150                 155                 160

Arg Ile Leu Ala Val Glu Arg Tyr Leu Lys Asp Gln Gln Leu Leu Gly
                165                 170                 175

Ile

<210> SEQ ID NO 7
<211> LENGTH: 345
<212> TYPE: PRT
<213> ORGANISM: Human immunodeficiency virus

<400> SEQUENCE: 7

Ala Val Gly Ile Gly Ala Leu Phe Leu Gly Phe Leu Gly Ala Ala Gly
 1               5                  10                  15

Ser Thr Met Gly Ala Ala Ser Met Thr Leu Thr Val Gln Ala Arg Gln
                 20                  25                  30

Leu Leu Ser Gly Ile Val Gln Gln Gln Asn Asn Leu Leu Arg Ala Ile
                 35                  40                  45
```

```
Glu Ala Gln Gln His Leu Leu Gln Leu Thr Val Trp Gly Ile Lys Gln
 50                  55                  60

Leu Gln Ala Arg Ile Leu Ala Val Glu Arg Tyr Leu Lys Asp Gln Gln
 65                  70                  75                  80

Leu Leu Gly Ile Trp Gly Cys Ser Gly Lys Leu Ile Cys Thr Thr Ala
                 85                  90                  95

Val Pro Trp Asn Ala Ser Trp Ser Asn Lys Ser Leu Glu Gln Ile Trp
            100                 105                 110

Asn His Thr Thr Trp Met Glu Trp Asp Arg Glu Ile Asn Asn Tyr Thr
            115                 120                 125

Ser Leu Ile His Ser Leu Ile Glu Glu Ser Gln Asn Gln Gln Glu Lys
        130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
            180                 185                 190

Ile Val Asn Arg Val Arg Gln Gly Tyr Ser Pro Leu Ser Phe Gln Thr
        195                 200                 205

His Leu Pro Thr Pro Arg Gly Pro Asp Arg Pro Glu Gly Ile Glu Glu
    210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
            260                 265                 270

Leu Leu Gly Arg Arg Gly Trp Glu Ala Leu Lys Tyr Trp Trp Asn Leu
        275                 280                 285

Leu Gln Tyr Trp Ser Gln Glu Leu Lys Asn Ser Ala Val Ser Leu Leu
    290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335

Arg Gln Gly Leu Glu Arg Ile Leu Leu
            340                 345

<210> SEQ ID NO 8
<211> LENGTH: 223
<212> TYPE: PRT
<213> ORGANISM: Schistosoma japonicum

<400> SEQUENCE: 8

Met Ala Cys Gly His Val Lys Leu Ile Tyr Phe Asn Gly Arg Gly Arg
 1               5                  10                  15

Ala Glu Pro Ile Arg Met Ile Leu Val Ala Ala Gly Val Glu Phe Glu
                 20                  25                  30

Asp Glu Arg Ile Glu Phe Gln Asp Trp Pro Lys Ile Lys Pro Thr Ile
             35                  40                  45

Pro Gly Gly Arg Leu Pro Ile Val Lys Ile Thr Asp Lys Arg Gly Asp
         50                  55                  60

Val Lys Thr Met Ser Glu Ser Leu Ala Ile Ala Arg Phe Ile Ala Arg
 65                  70                  75                  80
```

```
Lys His Asn Met Met Gly Asp Thr Asp Asp Glu Tyr Tyr Ile Ile Glu
                85                  90                  95
Lys Met Ile Gly Gln Val Glu Asp Val Glu Ser Glu Tyr His Lys Thr
            100                 105                 110
Leu Met Lys Pro Pro Glu Glu Lys Glu Lys Ile Ser Lys Glu Ile Leu
        115                 120                 125
Asn Gly Lys Val Pro Ile Leu Leu Gln Ala Ile Cys Glu Thr Leu Lys
    130                 135                 140
Glu Ser Thr Gly Asn Leu Thr Val Gly Asp Lys Val Thr Leu Ala Asp
145                 150                 155                 160
Val Val Leu Ile Ala Ser Ile Asp His Ile Thr Asp Leu Asp Lys Glu
                165                 170                 175
Phe Leu Thr Gly Lys Tyr Pro Glu Ile His Lys His Arg Lys His Leu
            180                 185                 190
Leu Ala Thr Ser Pro Lys Leu Ala Lys Tyr Leu Ser Glu Arg His Ala
        195                 200                 205
Thr Ala Phe Leu Val Pro Arg Gly Ser Pro Gly Ile His Arg Asp
    210                 215                 220

<210> SEQ ID NO 9
<211> LENGTH: 287
<212> TYPE: PRT
<213> ORGANISM: HIV and Schistosoma japonicum hybrid

<400> SEQUENCE: 9

Met Ala Cys Gly His Val Lys Leu Ile Tyr Phe Asn Gly Arg Gly

-continued

```
225                 230                 235                 240

Ile Trp Asn His Thr Thr Trp Met Glu Trp Asp Arg Glu Ile Asn Asn
                245                 250                 255

Tyr Thr Ser Leu Ile His Ser Leu Ile Glu Glu Ser Gln Asn Gln Gln
            260                 265                 270

Glu Lys Asn Glu Gln Glu Leu Leu Glu Leu Asp Lys Trp Ala Ser
            275                 280                 285
```